United States Patent [19]

Knifton

[11] Patent Number: 5,169,992

[45] Date of Patent: Dec. 8, 1992

[54] BISPHENOL A PRODUCTION USING ACIDIC CLAY CATALYSTS

[75] Inventor: John F. Knifton, Austin, Tex.

[73] Assignee: Texaco Chemical Company, White Plains, N.Y.

[21] Appl. No.: 870,973

[22] Filed: Apr. 20, 1992

[51] Int. Cl.$^5$ .................. C07C 37/20; C07C 39/16
[52] U.S. Cl. .................. 568/727; 568/722; 568/728
[58] Field of Search .................. 568/722, 727, 728

[56] References Cited

U.S. PATENT DOCUMENTS 1,977,627 10/1934 Greenhalgh .................. 568/728
1,978,949 10/1934 Kohn et al. .................. 568/728
3,496,239 2/1970 Hamilton et al. .................. 568/728
4,777,301 10/1988 Olson .................. 568/727

FOREIGN PATENT DOCUMENTS 0331173 9/1989 European Pat. Off. .................. 568/727
0116357 10/1978 Japan .................. 568/727

Primary Examiner—Werren B. Lone
Attorney, Agent, or Firm—Jack H. Park; Kenneth R. Priem; Cynthia L. Kendrick

[57] ABSTRACT

Disclosed is a one step method for synthesis of bisphenol A which comprises reacting phenol with acetone in the presence of a catalyst comprising an acidic montmorillonite clay having the structure:

$$M_{x/n}{}^{n+} \cdot yH_2O(Al_{4-x}Mg_x)(Si_8)O_{20}(OH)_4$$

where M represent the interlamellar, balancing cation (normally sodium or lithium), and x, y and n are integers, wherein the acidic clay has been pretreated with an acid and optionally has deposited thereon an acid selected from the group consisting hydrogen fluoride, a fluorosulfonic acid or a mineral acid, at a temperature of from 20° C. to 200° C. and a pressure of from near atmospheric to about 1000 psi.

15 Claims, No Drawings

BISPHENOL A PRODUCTION USING ACIDIC CLAY CATALYSTS

FIELD OF THE INVENTION

This invention relates to methods of producing bisphenol A. More particularly, it relates to a method of producing bisphenol A from acetone and phenol using montmorillonite clay modified with an acid selected from the group consisting of sulfuric acid, hydrogen fluoride treated clays and trifluoromethane sulfonic acid-treated clays.

BACKGROUND OF THE INVENTION

The reaction of phenol and acetone over a catalyst to produce bisphenol A is known in the art. Catalysts which have been used include cation exchange resins and acids.

Generally, the use of acids represents the older method for the condensation of phenol with acetone. Representative acids include an aromatic sulfonic acid (German Offen 2,811,182 and U.S. Pat. No. 4,387,251), a volatile acid catalyst (U.S. Pat. No. 2,623,908), a strong mineral acid such as HCl or $H_2SO_4$ (U.S. Pat. No. 2,359,242), hydrochloric acid (U.S. Pat. No. 4,517,387), $H_2SO_4$ or HCl and 2-(4-pyridyl)ethanethiol (Japanese Kokai-57-118528), concentrated HCl (Japanese Kokai 60-38335) and hydrogen chloride (U.S. Pat. No. 4,169,211).

Acidic mineral catalysts have several disadvantages. They necessitate construction materials which are considerably more expensive, they represent more of an environmental impact due to the cogeneration of waste materials and product purification is more costly.

A number of cation exchange resins have been used to convert phenol and acetone to bisphenol A. Representative catalysts are described in the following patents which are assigned to GE:

In U.S. Pat. No. 4,590,303, the cation exchange catalyst is a poly(styrene-divinylbenzene) copolymer which is partially modified by reacting the acidic groups with mercaptoalkylamines. Acetone conversions of 48-65% are observed.

In European Patent No. 144,735, the catalyst is a sulfonated polystyrene ion exchange resin having ionically bound (25-35 mol%) N-alkylamino-organomercaptan groups. Acetone conversions of 50-70% are observed.

U.S. Pat. No. 4,455,409 discloses an aromatic organic resin having amino-organomercaptan groups attached to 5-25% of the sulfonyl radicals by covalent nitrogen-sulfur linkages. Acetone conversion of 50% is observed.

U.S. Pat. No. 4,424,283 discloses a method for making leach resistant organoaminomercaptan substituted sulfonated aromatic organic polymers which demonstrate acetone conversions of 40-72%.

U.S. Pat. No.4,400,555 discloses a 2-mercaptoethylamine-modified, sulfonated, polystyrene divinylbenzene ion exchange resin situated in a series of reactors. Overall acetone conversion was 66%. In related U.S. Pat. No.4,391,997, the same catalyst is modified with mercaptoalkylamine.

A cation exchange catalyst comprising aromatic sulfonyl units substituted with an N-alkylamino-organomercapto radical was employed in U.S. Pat. No.4,396,728. In U.S. Pat. No.4,375,567 phenol was condensed with acetone over a sulfonated polystyrene ion exchange modified with mercaptan. U.S. Pat. No.4,365,099 discloses pretreatment of phenol with a chelating resin.

A number of patents assigned to Mitsubishi Chemicals also disclose resins for conversion of phenol and acetone to bisphenol A:

U.S. Pat. No.4,478,956 discloses a sulfonic acid type cation exchanger resin partially modified with a pyridine alkanethiol.

In Japanese Kokai 59-170031, a Diaion ® SK-104 catalyst was added to a reactor as a suspension layer.

Japanese Kokai 57-85335 discloses the use of a sulfonic acid-type cation exchange resin partially modified with 2,2-bis[2-(4-pyridyl)ethylthio]propane where the phenol is pretreated with Diaion ® SK-104.

In Japanese Kokai 57-72927, the resin is a sulfonic acid-type cation exchange resin modified with a mercaptan compound.

A different approach was taken in Japanese Kokai 61-78741, assigned to Mitsui Toatsu Chemicals using 5 parts of Lewatit ® SC-102 and 10 parts of Molecular Sieve 5A.

In patents assigned to Shell, catalysts for bisphenol A reactions include sulfonic acid groups neutralized with an aminothiooarboxylio acid or ester or a thiazolidine compound (British 1,539,186), an acid ion exchange resin in the metal salt form modified with a mercaptan compound (U.S. Pat. No.4,191,843) and a cation exchange resin having sulfonic acid groups wherein amino thiophenol is used to bind directly to the aromatic nucleus (U.S. Pat. No.4,045,379).

The following references give an overview of catalysts which have been used to convert phenol and acetone to bisphenol A.

U.S. Pat. No.4,590,303—Poly(styrene-divinylbenzene) copolymers;

ED 144,735—Sulfonated polystyrene ion exchange resin ionically bound with N-alkylamino-organomercaptan groups;

U.S. Pat. No.4,455,409—Amino-organomercaptan groups attached to sulfonyl halides;

U.S. Pat. No.4,424,283—Organoaminomercaptan substituted sulfonated aromatic organic polymers;

U.S. Pat. No.4,391,997—2-Mercaptoethylamine modified sulfonated polystyrene divinyl benzene;

U.S. Pat. No.4,396,728—A cation exchange catalyst comprising aromatic sulfony units substituted with an N-alkylamino-organomercapto radical;

U.S. Pat. No.4,478,956—A sulfonic acid type cation exchange resin partially modified with a pyridine alkanethiol;

Japanese Kokai 59-170031—A Diaion ® SK-104 catalyst;

Japanese Kokai 57-85335—A sulfonic acid-type cation exchange resin partially modified with 2,2-bis[2-4-pyridyl)ethylthio]propane;

Japanese Kokai 57-72927—A sulfonic acid-type cation exchange resin modified with a mercapto compound;

British 1,539,186—Sulfonic acid groups neutralized with an aminothiocarboxylic acid or a thiazolidine compound;

U.S. Pat. No.4,191,843—An ion exchange resin in the metal salt form modified with a mercaptan compound;

U.S. Pat. No.4,045,379—A cation exchange resin having sulfonic acid groups where amino thiophenol is used to bind directly to the aromatic nucleus.

The use of clays as catalysts for selected applications is known in the art. In an article titled "Catalysis: Selective Developments", Chem. Systems Report 84-3, 239-249, section 3.4320, the unusual properties of smectite clays which make them of interest as catalysts are discussed. These compositions are layered and exhibit a 2:1 relationship between tetrahedral and octahedral sites. In addition the combination of cation exchange, intercalation and the fact that the distance between the layers ca be adjusted provide interesting possibilities.

An article by F. Figueras, titled "Pillared Clays as Catalysts", in Catal. Rev.-Sci. Eng., 30, 457 (1988) discusses methods of modifying clays and the effects of the modifications. At page 472, there is a discussion of the method of drying, i.e. air drying or freeze drying, which can affect the macroporosity of the resulting product and, as expected, the adsorption capacity. The author concludes the thermal stability of pillared clays can be improved to reach 800° C. using information available with respect to intercalation and drying methods.

Figueras notes, page 481, that the acid strength of montmorillonites wa found to be higher than that of Y-zeolites and, in the case of the clays, Bronsted acidity appears to be weaker than Lewis acidity. The author describes three kinds o acid sites known to exist at the surface of clay and suggests the coexistence of several types of acidity makes the localization of acid sites more difficult than in well-crystallized structures.

There are two reviews of the catalytic activity of pillared clays by T. Matsuda and E. Kikuchi, titled "Acidic Properties of Pillared Clays in Relation to Their Catalytic Behavior", in Proceedings of International Symposium on Acid-Base Catalysis, Sapporo, Nov. 28-Dec. 1, 1988. In Ch. 3.11 these Catalyst authors observed Bronsted acid sites are responsible for isomerization whereas both Bronsted and Lewis acid sites can catalyze disproportionation. Other pertinent findings were that Bronsted sites are far more active than Lewis sites, however, studies would indicate an irreversible change of Bronsted acidity to Lewis acidity in the course of high temperature calcination, ibid, page 354. They concluded that cracking of a compound such as cumene, for example, depended only on the acidic properties, however disproportion activity was affected by the pore structure in addition to acidity. This was thought to relate to the fact that pillared montmorillonite had regular micropores while pillared saponite consisted of macropores. In addition saponite is tetrahedrally charged clay with Al cations substituting for Si cations. In montmorillonite, in contrast, Mg cations are octahedrally substituted for Al cations. At page 352, it is stated that cracking activity is satisfactorily related to Bronsted acidity while it is difficult to find any relationship between the disproportionation activity and the acidic property.

In British Patent GB 1,265,152 ortho-alkylated phenols were prepared in about 52% yield using Fulmont at 300° C. with a small amount of sulfuric acid. In German Patent 2,552,175, KSF was the catalyst and about 15% para-product was formed.

There are two reviews of the use of pillared, cation-exchanged and acid-treated montmorillonite as catalysts for certain organic reactions by J. M. Adams et al., J. Inclusion Phenomena, 5, 663 (1987), Applied Clay Science, 2, 309 (1987). These clays display Bronsted and Lewis acid activities. It is noted that while some cationic species are stable in solution over a wide concentration and pH range, others are not, particularly solutions containing aluminum. It is noted that it is difficult to ensure a reproducible $Al^{3+}$ clay and moreover, since workers have used slightly different exchanging and washing procedures, a comparison between related experiments is hindered. Commercial acid-treatment is carried out using concentrated hydrochloric, sulphuric or phosphoric acids. The concentration of the acid and the time of the treatment is variable. Sometimes the excess acid is removed by washing, whereas in other products this is not the case. Therefore there is a great variety in the type and activity of acid-treated clays.

Montmorillonites have been used as catalysts for the reaction of straight chain alk-1-enes to ethers, and for alkenes plus alcohols. In the latter, primary alcohols gave high yields, secondary less and tertiary alcohols only trace amounts. The $Al^{+3}$ clays have efficiencies of one third to one half of Amberlyst ® 15 in reactions of this type without solvent or using 1,4-dioxane.

The acid-treated clay K-306 can be used to convert methanol and ammonia to methylamines. Acid-treated clays have also been used to convert cumene hydroperoxide to phenol and acetone.

With respect to the production of bisphenol A most of the recent research and development has been concerned with BPA separation and purification. There is an increasing demand for high purity bisphenol A in polycarbonate resin manufacture. Catalyst enhancement is also of interest, see: "Bisphenol A and Alkylated Phenols," SRI PEP Report No. 192 (Dec. 1988) Section 4.

Processes using acid catalysts, such as anhydrous HCl, require extensive recovery facilities, product purification and waste treatment. In addition, the presence of highly corrosive streams requires the use of costly conversion-resistant construction materials.

The newer processes using a cation exchange resin catalyst have an advantage over the acid catalysts in that the resins are non-corrosive and require no catalyst recovery, Ibid, p. 5-1.

Though they represent an advance over the use of acid catalysts, the resins still have disadvantages. In a typical resin process design, the process unit is divided into three sections, condensation, separation and rearrangement and the operation of the condensation reactor is limited to <120° C. due to the low thermal stability of said resins. There is a necessity for extensive recycling of unreacted phenol/acetone, water removal, crystallization and purification.

It would be a distinct advance in the art if bisphenol A could be prepared in one unit using a more thermally and hydrolytically stable catalyst which did not require phenol/acetone recycling, pretreatment of the feed for water removal, etc. It would also be desirable if it did not use corrosive chemicals or require by-product salt handling an disposal. It would be particularly helpful commercially if the catalyst exhibited high thermal stability and extended catalyst life. Such a process would be especially attractive since it would be simpler to operate than processes currently used in the art.

It is an object of the instant invention to provide a one-step process for the synthesis of bisphenol A using a catalyst system which accomplishes the reaction in one step and exhibits extended life.

SUMMARY OF THE INVENTION

In accordance with the foregoing the novel process of the instant invention for preparing bisphenol A comprises reacting a phenol with the acetone in the presence of a catalyst comprising an acidic montmorillonite clay treated with an acid selected from the group consisting of hydrogen fluoride, a fluorosulfonic acid or anhydride, and a mineral acid, at temperatures of from about 20° C. to 200° C.

DESCRIPTION OF THE PREFERRED EMBODIMENT

Preparation of the product of this invention may be carried out typically by reacting an excess of phenol with acetone in the presence of an acidic clay. The reaction can be represented by the following:

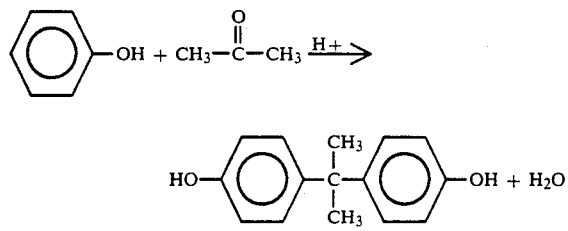

The product bisphenol A is isolated in high purity by fractional distillation. Bisphenol A is an important specialty chemical. Bisphenol A is in demand as a raw material for manufacturing polycarbonate and epoxy resins. The polycarbonate resins are used for glazing, computer housings, electric parts, compact disks and appliances. Epoxy resins are used for surface coatings, laminates, composites, adhesives, moldings and castings.

The molar ratio of the acetone to phenol feed mix can vary from about 10:1 to 1:100. The preferred molar ratio is about 1:10.

As stated the catalyst comprises an inorganic clay which is acid activated and modified with an acid selected from the group consisting of hydrogen fluoride, fluorosulfonic acids and anhydrides, and sulfuric acid, plus combinations thereof. Suitable fluorosulfonic acids or anhydrides include fluorosulfonic acid, trifluoromethanesulfonic acid (triflic acid) and trifluoromethanesulfonic anhydride.

The inorganic clays which ma be used to effect this reaction are preferably silica and alumina-rich smectite clay catalysts. A variety of clay catalysts containing alumina and silica are effective in the subject reaction, however it is necessary that the alumina or silica be acidic under normal operating conditions. A group of catalysts which works well in this synthesis are acidic clay mineral catalysts. Chemically clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in the reaction of Equation 1 are smectite clays. Smectite clays are discussed in the article cited in Chem Systems Report, 84-3. These clays have small particle size and unusual intercalation properties which afford them high surface area. They are alumino silicates with a unique structure that permits modifications which provide useful catalysts. They comprise layered sheets of octahedral sites between sheets of tetrahedral sites, and the distance between the layers can be adjusted by swelling, through treatment with the appropriate solvent, or treatment with a pillaring or Lewis acid reagent etc. What renders the smectites of particular interest among the clay minerals is their combination of cation exchange, intercalation and swelling properties.

The three-layer sheet types of smectite clay include montmorillonite, vermiculite and certain micas, all of which may be expanded between their layers by the appropriate treatment. The idealized basic structure of clays of this type is that of a pyrophyllite which has the basic formula $Si_8Al_4O_{20}(OH)_4$.

A general representation of the montmorillonite structure is:

$$M_{x/n}{}^{n+} \cdot yH_2O(Al_{4-x}Mg_x)(Si_8)O_{20}(OH)_4$$

where M represents the interlamellar, balancing cation (normally sodium or lithium), and x, y and n are integers.

These montmorillonite clays are best used in the present application in an acidic form. Acids activate montmorillonites by attacking and solubilizing structural cations in the octahedral layers. This opens up the clay structure and increases surface area. These acid-treated clays act a strong Bronsted acids. Generally strong mineral acids are used to activate the clay, such as, for example, sulfuric acid and phosphoric acid. As noted in the Matsuda reference, supra, there is an indication Bronsted sites are more active, but have a tendency to convert to Lewis acid sites as temperature increases during calcination of pillared clays. The clays are effective in the form of granules, powders or extrudates.

The acid-treated montmorillonite clays of the present invention upon which the triflic acid or hydrofluoric acid are deposited should have acidities of 1.0 or greater mg KOH/gm, and preferably 5 to 100 mg KOH/gm, titrated to a phenolphthalein end point. Their surface area should be $\geq 30$ m$^2$/g, and preferably 200 to 1000 m$^2$/g. Their moisture content should be limited also, whereby upon heating to 220° F., the weight loss is generally less than 20 wt%, but may be higher under certain circumstances.

Illustrative examples of suitable acidic montmorillonite clays include clays in granular form, such as Filtrol grade 24, having a 20-60 mesh size, and Grade 24 Superacid Clays. Filtrol grade 24 is manufactured by Engelhard and has an acid capacity of 25 mg KOH/g. Grade 24 Superacid Clays, also from Engelhard, typically have acidities of 33-93 mg KOH/g.

Where the montmorillonite clay or acid-pretreated montmorillonite clay, as described above, is impregnated with triflic acid or hydrogen fluoride, the clay is generally treated with from 0.01% to 10% triflic acid or HF and preferably the clay is impregnated with from about 0.1% to 1.0% triflic acid. The instant examples demonstrate that about 0.1% to 1.0% is an effective amount.

Where hydrogen fluoride is deposited on acidic montmorillonite about 0.1% to 10% is a preferred effective amount.

An effective amount of triflic acid would be sufficient to produce an acidity of the catalyst in the range of 1-100 mg KOH/g. An effective amount of hydrogen fluoride would be sufficient to produce a catalyst acidity in the range of 1 to 100 mg KOH/g.

Preparation of bisphenol A is conducted in a fixed bed, continuous flow reactor, operated upflow.

The temperature of the reactor can be in the range of 20°-200° C. and preferably 30° C. to 140° C. The preferred temperature depends on the choice of conditions, etc., however, a most effective temperature is about 110°-130° C. The pressure can be in the range of atmospheric to 1000 psi and is preferably about 300 psi.

Typically the bisphenol A is generated continuously in up to ca. 10+ wt% concentration in the crude product liquid effluent.

Acetone and phenol conversions are significant. Fractional distillation yielded pure bisphenol A wherein two isomers are present in a ratio of about 3 to 1.

These yields are achieved at a total liquid hourly space velocity (LHSV) of one to 10 under mild conditions.

Here LHSV is defined as follows:

$$LHSV = \frac{\text{Volume of Total Liquid Feed Run Through the Reactor Per Hour}}{\text{Volume of Catalyst in Reactor}}$$

Conversion of acetone and phenol (wt%) is estimated in the following examples using the equation:

$$100 - \left( \frac{\text{Wt \% Conc. of Acetone or Phenol in Product}}{\text{Wt \% Conc. of Acetone or Phenol in Feed}} \right) \times 100$$

Yields of bisphenol A (mole%) are estimated from:

$$\frac{\text{Moles of Bisphenol A in Product Liquid}}{\text{Moles of Acetone or Phenol in Feed}} \times 100$$

THE ACCOMPANYING EXAMPLES ILLUSTRATE

1) The Synthesis of a trifluoromethanesulfonic acid-treated montmorillonote clay (Example 1).
2) The synthesis of bisphenol A from phenol and acetone using a sulfuric acid-treated clay catalyst over a range of operating temperatures (Example 2).
3) The synthesis of bisphenol A from phenol and acetone using a series of other acidic clay catalysts, e.g.:
   a) A trifluoromethanesulfonic acid-treated clay (Example 3).
   b) A HF-treated clay (Example 4).
   c) Another sulfuric acid-treated clay (Example 5).
   Here, using a 10:1 molar feed mix of phenol to acetone, bisphenol A is generated in up to 10.4 wt% concentration in the crude product mix (see data in Table IV and Example 5).
4. Extended catalyst life in bisphenol A service is illustrated in Example 6 for a sulfuric acid-treated clay.
5. Isolation of pure bisphenol A from the crude product effluent is illustrated in Example 3.

Product analyses were primarily by gas liquid chromatography (glc) and gel permeation chromatography (gpc).

The examples which follow illustrate the generation of bisphenol A from phenol and the acetone using acidic montmorillonite clays modified with specified acids. These examples are only intended as a means of illustration and it should be understood the invention is not meant to be limited thereby.

EXAMPLE 1

This example illustrates the preparation of a trifluoromethanesulfonic acid-modified montmorillonite clay.

To 85g of a neutral montmorillonite clay (Engelhard Grade 2C powder, dried at 175° C. in vacuo) was added a solution of trifluoromethanesulfonic acid (10.0g) in dried acetone (100cc). The mixture was stirred for 24 hours under a nitrogen blanket, filtered and the solids washed first with acetone and water, then dried in vacuo at 40° C. overnight and at 150° C. for 4 hours.

The recovered pale yellow powder was found to contain by analysis:

$H_2O = 0.73\%$

Acidity = 10.6 mg KOH/g

EXAMPLE 2

This example illustrates the production of bisphenol A from phenol and acetone using a sulfuric acid-treated montmorillonite clay catalyst.

Synthesis was conducted in a 150cc capacity tubular reactor constructed of 316 stainless steel, operated upflow and mounted in a furnace, controllable to ±1.0° C. and fitted with liquid feed pumps, a pressure regulating device and equipment for monitoring temperature, pressure and flow rate.

The reactor was charged at the beginning of the experiment with 150cc of a sulfuric acid-treated montmorillonite clay, in granular form (Sample 104589 from Engelhard) having a titratable acidity of 33 mq KOH/g. The catalyst bed was then treated with a phenol/acetone (10:1 molar mix) upflow, at a rate of 150 cc/hour, while the reactor was held at 50° C., with a total pressure of 300 psi. Samples of crude products effluent were collected on stream, analyzed by glc and gpc. Typical analyses data are summarized in Table I.

Catalyst performance over a range of temperatures (50°-110° C.) was also measured, after reaching equilibrium conditions. Summary data for these additional runs are also given in Table I.

Finally, samples of each product were stripped under vacuum to remove lights plus unreacted acetone, then reanalyzed for bisphenol A content by gpc. These data are also included in Table I.

EXAMPLES 3-5

Following the procedures and practices of Example 2, the synthesis of bisphenol A from phenol and acetone was demonstrated using the following acidic clay catalysts:

a) A montmorillonite clay that had been treated with trifluoromethanesulfonic acid (triflic acid) such that the concentration of triflic acid (TF) on the formulated catalyst was 0.1% and the titratable acidity was 11 mg KOH/g.
b) A hydrogen fluoride (HF) treated clay that had previously been treated with sulfuric acid where the HF concentration of the finished catalyst was ca. 4.5%.
c) Another sulfuric acid-treated montmorillonite clay with a titratable acidity of 93 mg KOH/g.

The glc and gpc analyses of the crude product effluent products and stripped products from these three experiments are summarized in the accompanying Tables II→IV.

Fractional distillation of the crude product liquid from Example 3, in vacuo, yielded pure bisphenol A. NMR and IR analyses of this bisphenol A fraction showed the I to II isomer ratio to be 74/26.

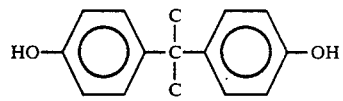

Synthesis procedures were as described in Example 2. The continuous reactor system was charged with 150cc of sulfuric acid-treated montmorillonite clay that had previously been dried in vacuo at 175° C. having a titratable acidity of 45 mg KOH/g and a water content of 0.3% A feed mix of phenol/acetone (10:1 molar) was passed upflow over said catalyst at a rate of 150 cc/hour, at 130° C. and a total pressure of 300 psi. Samples of crude product effluent were collected on stream, analyzed by glc and gpc. The results are summarized in Table V.

TABLE I

| | | | | | bisphenol A Stripped Product Conc (%) | | ←Crude Product Conc (%)→ | | | |
|---|---|---|---|---|---|---|---|---|---|---|
| | | | | | | | gpc | | glc | |
| Ex. | Catalyst | Operating Temp. (°C.) | LHSV | Sample | BPA | PhOH | BPA | PhOH | Ac₂O | PhOH |
| 1 | H₂SO₄/Clay | 50 | 1 | 1 | 0.74 | 99.3 | | | | |
| | | 70 | 1 | 2 | 1.41 | 98.6 | | | | |
| | | 70 | 1 | 3 | 1.15 | 98.9 | 0.71 | 99.3 | 7.8 | 92.1 |
| | | 90 | 1 | 4 | 3.03 | 97.0 | 2.87 | 97.1 | 7.7 | 92.1 |
| | | 110 | 1 | 5 | 7.74 | 92.3 | 6.45 | 93.6 | 5.9 | 93.8 |
| | | | | FS | | | | | 10.2 | 89.7 |

TABLE II

| | | | | | bisphenol A Stripped Product Conc (%) | | ←Crude Product Conc (%)→ | | | |
|---|---|---|---|---|---|---|---|---|---|---|
| | | | | | | | gpc | | glc | |
| Ex. | Catalyst | Operating Temp. (°C.) | LHSV | Sample | BPA | PhOH | BPA | PhOH | Ac₂O | PhOH |
| 3 | TF/Clay | 50 | 1 | 1 | | | 0.3 | 99.7 | 8.0 | 91.9 |
| | | 70 | 1 | 2 | 1.3 | 98.7 | 1.2 | 98.8 | 7.7 | 92.1 |
| | | 90 | 1 | 3 | 3.9 | 95.8 | 3.3 | 96.7 | 7.7 | 92.2 |
| | | 110 | 1 | 4 | 6.9 | 93.2 | 5.9 | 94.1 | 6.6 | 93.2 |
| | | 130 | 1 | 5 | 8.9 | 91.1 | 8.2 | 91.9 | 6.1 | 93.2 |
| | | | | FS | | | | | 7.8 | 92.2 |

TABLE III

| | | | | | bisphenol A Stripped Product Conc (%) | | ←Crude Product Conc (%)→ | | | |
|---|---|---|---|---|---|---|---|---|---|---|
| | | | | | | | gpc | | glc | |
| Ex. | Catalyst | Operating Temp. (°C.) | LHSV | Sample | BPA | PhOH | BPA | PhOH | Ac₂O | PhOH |
| 4 | HF/H₂SO₄/Clay | 50 | 1 | 1 | | | | 100 | 7.4 | 92.6 |
| | | 70 | 1 | 2 | | | 0.1 | 99.9 | 7.0 | 93.0 |
| | | 90 | 1 | 3 | | | 0.6 | 99.5 | 6.9 | 93.1 |
| | | 110 | 1 | 4 | | | 1.9 | 98.1 | 6.6 | 93.3 |
| | | 130 | 1 | 5 | 4.4 | 95.6 | 4.3 | 95.8 | 6.2 | 93.6 |
| | | | | FS | | | | | 7.4 | 92.6 |
| 5 | H₂SO₄/Clay | 50 | 1 | 1 | | | 0.1 | 99.9 | 5.6 | 94.2 |
| | | 70 | 1 | 2 | | | 1.0 | 99.0 | 7.4 | 92.5 |
| | | 90 | 1 | 3 | 4.1 | 97.2 | 3.5 | 96.5 | 6.3 | 93.6 |
| | | 110 | 1 | 4 | 8.1 | 91.9 | 7.2 | 92.8 | 5.7 | 94.1 |
| | | 130 | 1 | 5 | 11.4 | 88.6 | 10.4 | 89.6 | 5.7 | 94.1 |
| | | | | FS | | | | | 7.3 | 92.6 |

Structure I

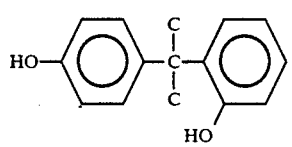

Structure II

EXAMPLE 6

This example illustrates an extended catalyst life for a sulfuric acid-treated clay catalyst.

TABLE V

| | | | | bisphenol A Product Composition (gpc, %) | |
|---|---|---|---|---|---|
| Ex. | Catalyst | Sample | Time On Stream (Days) | BPA | PhOH |
| 6 | H₂SO₄/Clay | 1 | 3 | 6.3 | 93.7 |
| | | 3 | 7 | 4.0 | 96.0 |
| | | 4 | 10 | 3.5 | 96.5 |
| | | 6 | 15 | 2.3 | 97.7 |
| | | 7 | 18 | 2.2 | 97.8 |

What is claimed is:

1. A one step method for synthesis of bisphenol A which comprises reacting phenol and acetone in the presence of a catalyst comprising montmorillonite clay having the structure:

$$M_{x/n}{}^{n+}\cdot yH_2O(Al_{4-x}Mg_x)(Si_8)O_{20}(OH)_4$$

where M represents the interlamellar, balancing cation (normally sodium or lithium), and x, y and n are integers, at a temperature of from 20° C. to 200° C. and a pressure of near atmospheric to about 1000 psi wherein the clay is acidic from pretreatment with an acid selected from the group comprising hydrogen fluoride, fluorosulfonic acids or anhydrides, or mineral acids, as well as combinations thereof.

2. The method of claim 1 wherein the mineral acid used to acid activate the clay is sulfuric acid.

3. The method of claim 2 wherein the montmorillonite clay is treated with sulfuric acid and has an acidity of 1.0 or greater mg KOH/gm.

4. The method of claim 1 wherein the montmorillonite clay is treated with hydrogen fluoride.

5. The method of claim 2 wherein the acidity of the sulfuric acid-treated clay is in the range of 5–100 mg KOH/g.

6. The method of claim 2 wherein the sulfuric acid-treated montmorillonite clay has deposited thereon 0.01% to 10% wt% hydrogen fluoride.

7. The method of claim 2 wherein the sulfuric acid-treated montmorillonite clay has deposited thereon 4.5% by weight hydrogen fluoride.

8. The method of claim 4 wherein the acidity of the hydrogen fluoride treated clay is in the range of 1 to 100 mg KOH/g.

9. The method of claim 1 wherein the fluorosulfonic acid is selected from the group comprising fluorosulfonic acid and triflic acid.

10. The method of claim wherein the montmorillonite clay has deposited thereon 0.01% to 10% wt% triflic acid.

11. The method of claim 9 wherein the montmorillonite clay has deposited thereon 0.1% by weight triflic acid.

12. The method of claim 9 wherein the acidity of the triflic acid-treated clay is in the range of 1–100 mg KOH/g.

13. The method of claim 9 wherein the fluorosulfonic anhydride is trifluoromethanesulfonic anhydride.

14. The method of claim 1 wherein the maximum operating temperature is in the range of 30° to 140° C.

15. The method of claim 1 wherein the acetone to phenol molar feed ratio is about 1 to 10.

* * * * *

UNITED STATES PATENT AND TRADEMARK OFFICE
CERTIFICATE OF CORRECTION

PATENT NO. : 5,169,992
DATED : December 8, 1992
INVENTOR(S) : John Frederick Knifton It is certified that error appears in the above-identified patent and that said Letters Patent is hereby corrected as shown below:

Claim 10, Col. 12, line 13, after "claim" insert --9 --.

Signed and Sealed this

Seventh Day of December, 1993

Attest:

BRUCE LEHMAN

Attesting Officer

Commissioner of Patents and Trademarks